US009242395B2

(12) United States Patent
Onofry et al.

(10) Patent No.: US 9,242,395 B2
(45) Date of Patent: Jan. 26, 2016

(54) PUNCH FOR POWDER PRESS

(71) Applicant: Kolmar Labs Group, Inc., Port Jervis, NY (US)

(72) Inventors: Craig Robert Onofry, Port Jervis, NY (US); Frank E. Casey, Milford, PA (US); Matthew M. Abbadessa, Sparrowbush, NY (US); Christopher G. Baker, Port Jervis, NY (US)

(73) Assignee: Kolmar Laboratories, Inc., Port Jervis, NY (US)

( * ) Notice: Subject to any disclaimer, the term of this patent is extended or adjusted under 35 U.S.C. 154(b) by 97 days.

(21) Appl. No.: 14/281,272

(22) Filed: May 19, 2014

(65) Prior Publication Data
US 2015/0328805 A1 Nov. 19, 2015

(51) Int. Cl.
*B29C 43/02* (2006.01)
*B30B 15/00* (2006.01)
*A61Q 1/12* (2006.01)
*B29C 43/00* (2006.01)
*B30B 15/06* (2006.01)
*B29L 31/00* (2006.01)
*A61K 8/02* (2006.01)

(52) U.S. Cl.
CPC .............. *B29C 43/003* (2013.01); *B30B 15/065* (2013.01); *A61K 8/022* (2013.01); *A61Q 1/12* (2013.01); *B29L 2031/772* (2013.01)

(58) Field of Classification Search
None
See application file for complete search history.

(56) References Cited

U.S. PATENT DOCUMENTS

| 4,962,627 A * | 10/1990 | Gueret ...................... B65B 1/24 53/412 |
| 5,039,294 A * | 8/1991 | Gautier ................. B30B 11/027 100/48 |
| 5,449,481 A | 9/1995 | Sagawa et al. |
| 2012/0139164 A1* | 6/2012 | Ishikawa ............... B30B 11/022 264/442 |

FOREIGN PATENT DOCUMENTS

| CA | 2 525 891 A1 | 12/2004 |
| JP | 2006-75852 A | 3/2006 |
| JP | 2010-36222 A | 2/2010 |

OTHER PUBLICATIONS

Machine Translation of JP2010036222A.
Machine Translation of JP2006-75852A.

* cited by examiner

*Primary Examiner* — Mary F Theisen
(74) *Attorney, Agent, or Firm* — Andrus Intellectual Property Law, LLP

(57) ABSTRACT

A punch for simultaneously pressing two or more different powder formulas has a punch body with a first region and second region. The first region is comprised of a first material and configured to apply a first predetermined pressure to a first powder formula when a ram force is placed on the punch body. The second region is at least partially comprised of a second material and is configured to apply a second predetermined pressure to a second powder formula when the ram force is placed on the punch body. The second material is less hard than the first material such that the second predetermined pressure is less than the first predetermined pressure.

20 Claims, 5 Drawing Sheets

PUNCH FOR POWDER PRESS

BACKGROUND

Currently available punches for pressing powder, such as cosmetic powder, consist of a solid block of metal, such as cold-rolled steel. Such punches are typically pressed onto a pan containing loose or lightly packed powder so as to achieve a particular hardness of a particular material. Such punches cannot be used to simultaneously compress more than one formula in a pan unless the formulas are highly similar or identical to one another because applying the single pressure from the punch to the two different formulas will result in different hardness characteristics and payoff performance.

For example, when pressing two different formulas contained within the same pan, the formula with more caking or pressing agent will press to a greater hardness than the formula with fewer caking or pressing agents. In such a scenario, the powder formula on one side of the pan will be much harder than the formula on the other side of the pan. The formula with more caking agents may become overly pressed, exhibit glazing, and/or yield insufficient payoff performance. The formula with less caking agents, on the other hand, may be under pressed, prone to dusting and breaking, and yield too much payoff performance.

Presently available systems and methods for pressing two or more formulas and containing them within the same pan involve separately pressing each formula in a separate plate to achieve a given hardness for each formula, and then combining the pressed formulas into a single pan where a finishing press is applied to smooth the edges of each formula and give the pan an appealing and unified look. Such systems and methods are time consuming, expensive, and error-prone, as each formula must be separately pressed and then removed from its initial container and placed in a new pan together with one or more other formulas that have also been pressed.

SUMMARY

The present inventors recognize that a punch is needed that enables simultaneous pressing of two or more formulas in a single pan using a standard mechanical or hydraulic powder press. Accordingly, the present inventors developed the punch disclosed herein allowing two or more formulas to be simultaneously pressed in the same pan.

A punch for simultaneously pressing two or more different powder formulas has a punch body with a first region and second region. The first region is comprised of a first material and configured to apply a first predetermined pressure to a first powder formula when a ram force is placed on the punch body. The second region is at least partially comprised of a second material and is configured to apply a second predetermined pressure to a second powder formula when the ram force is placed on the punch body. The second material is less hard than the first material such that the second predetermined pressure is less than the first predetermined pressure.

An embodiment of a cosmetic powder press for simultaneously pressing at least two different cosmetic formulas has a press device and a punch body. The press device has a press ram and is configured to exert the ram force. The punch body is positioned at the end of the press ram and has a first region comprised of a first material and configured to apply a first predetermined pressure to a first powder formula when the ram force is exerted on the punch body, and a second region comprised of a second material and configured to apply a second predetermined pressure to a second powder formula when the ram force is exerted on the punch body. The second material is less hard than the first material such that the second predetermined pressure is less than the first predetermined pressure.

A method of pressing two or more different cosmetic formulas contained adjacently in the same pan comprises dispensing a first powder formula into a first side of a divider in a pan and dispensing a second powder formula into a second side of the divider in the pan. The first powder formula and the second powder formula are then pre-pressed. The divider is then removed from the pan such that the first powder formula and the second powder formula are immediately adjacent to one another. The first powder formula and the second powder formula are then pressed in the pan with a punch body having a first region and a second region. The first region is comprised of a first material and configured to press the first formula, and the second region is comprised of a second material and is configured to press the second formula, wherein the second material is less hard than the first material.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION OF THE DRAWINGS

Figure 1A:
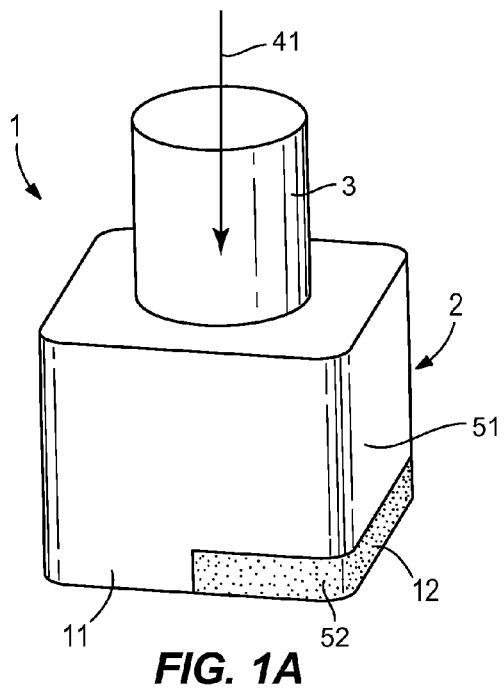
FIG. 1A depicts a side angle view of one embodiment of a punch for pressing two different powder formulas.

FIGS. 1 and 2 depict several possible embodiments of a punch for simultaneously pressing two or more different powder formulas contained in the same pan, or container. FIGS. 1A and 1B depict an embodiment of a punch 1 having a punch body 2 with a first region 11 comprised of a first material 51 and a second region 12 comprised partially of a second material 52. The punch 1 has a pressing face 9 that is pressed against a powder formula to achieve a given hardness of that formula. The punch 1 in the depicted embodiment has a stem 3 connected to the punch body 2.

Figure 3:
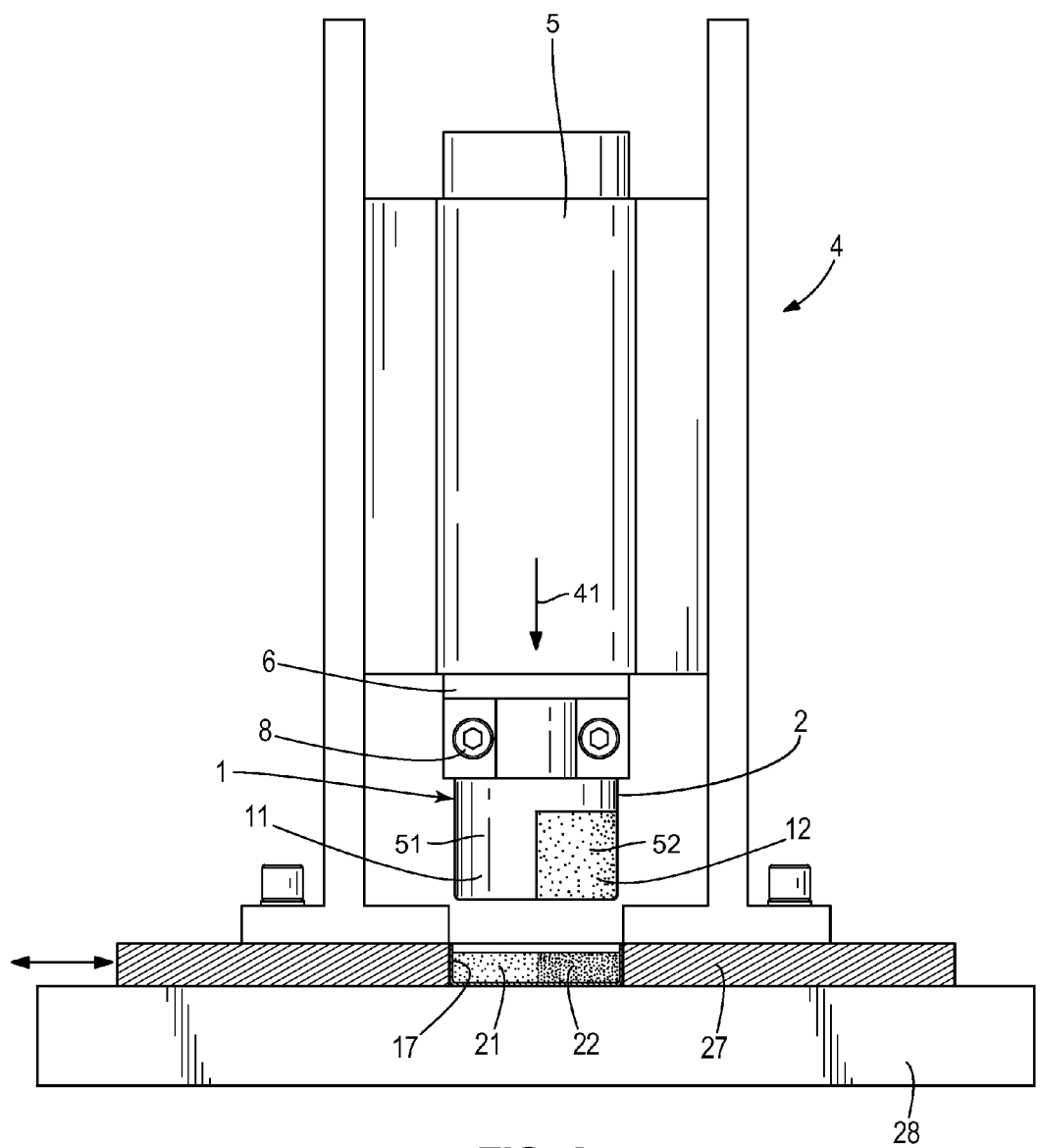
FIG. 3 depicts an embodiment of a powder press for simultaneously pressing two or more cosmetic formulas.

Turning briefly to FIG. 3, the punch 1 may be connected to a powder press 4, such as a cosmetic powder press configured to press cosmetic powder into a compact or a pressed form. The powder press 4 may have a press device 5 configured to move a press ram 6 to apply a ram force, for example to press a powder from a loose powder to a hardened powder. The punch 1 may have a stem 3 configured to connect with the press ram 6 at connection point 8. Such connection may be by any means known in the art, such as by one or more bolts, locking pins, or other connectors. Alternatively, the stem 3 and the connection point 8 may be threaded such that the stem 3 screws into the connector 8.

The punch 1 is configured such that when a ram force is applied on the punch body 2 by a press ram 6, the first region 11 and the second region 12 apply a different predetermined pressure to a pressed material. More specifically, the first region 11 and the second region 12 are comprised of two different materials that react differently to the ram force applied on the punch body 2 from the powder press 4. The difference in the pressure applied by, for example, the first region 11 and the second region 12 depends on the configuration of each region, such as differences in the first material 51 and the second material 52 as well as amount and configuration of each material in each region.

Returning to FIG. 1, the first material 51 and the second material 52 have different hardnesses, and therefore behave differently under force, such as the ram force applied by a powder press during a press action. In a preferred embodiment, the first material 51 is harder than the second material 52. In such an embodiment, when a downward ram force is applied on the punch body 2 in the direction of the arrow 41, the pressure applied on a material below the punch body by the first region 11 will be different than that applied by the second region 12. Namely, the force applied by the first region 11, which is comprised entirely of the harder first material 51, will be greater than the force applied by the second region 12, which is at least partially comprised of the second material 52. Thus, by varying the depth of the less hard second material 52 in the second region 12, different pressures can be applied by the second region 12.

Figure 1C:
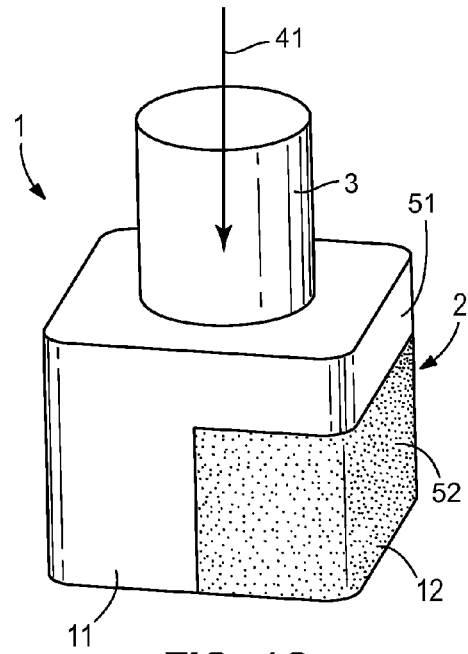
FIG. 1C depicts the side angle view of another embodiment of a punch for pressing two different powder formulas.
Figure 1B:
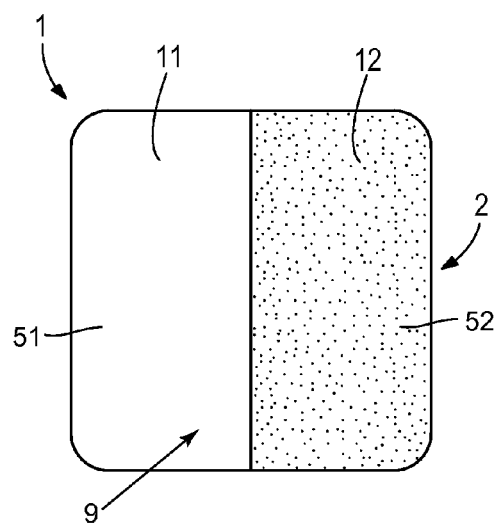
FIG. 1B depicts a bottom view of the embodiment of FIG. 1A.
Figure 1D:
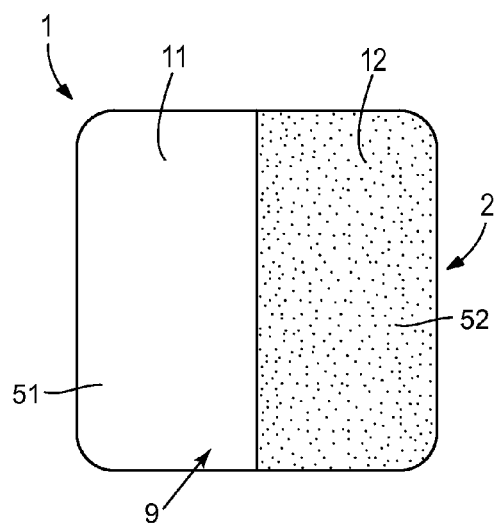
FIG. 1D depicts a bottom view of the embodiment of FIG. 1C.

Comparing the embodiments of FIGS. 1A-1B to that of FIGS. 1C-1D, the second region 12 may be configured to have more or less of the second material 52 in order to achieve a desired predetermined pressure. The second region 12, and any additional regions, may be comprised of only a thin strip of the second material 52, in which case the pressure applied by the second region would be only slightly less than that of the first. On another extreme, the second region 12 may be comprised entirely of the second material 52, in which case the pressure applied by the second region may be significantly less than that of the first (depending on the hardness of the second material 52 compared to the first material 51). For example, in the embodiment of FIG. 1A the second material 52 is less deep, or smaller from top to bottom, than that of the embodiment shown in FIG. 1C. Thus, the punch embodiment depicted in FIG. 1A has a harder second region 12 than the second region 12 of the punch embodiment depicted in FIG. 1C, and the second region 12 of the embodiment in FIG. 1A will exert more pressure to press the second powder formula 22 than the second region 12 of the embodiment depicted in FIG. 1C.

In the embodiment of FIG. 3, the powder press 4 may be comprised of any press device 5, which is any mechanism capable of exerting a ram force on the press ram 6, and thereby on the punch 1, in order to press a powder. For example, the press device 5 may be a hydraulic press or a mechanical press. The ram force exerted by the press device 5 is translated through a press ram 6 of the press device 5 to the punch 1 to press two or more different cosmetic formulas contained in the pan 17. A first powder formula 21 and a second powder formula 22 are contained in an undivided fashion within the pan 17, which is positioned below the punch 1. In other words, the pan 17 contains the first powder formula 21 and the second powder formula 22, which are immediately adjacent to one another without any divider therebetween. The pan 17 is positioned under the punch 1 by a die plate 27 with a hole cut therein to contain the pan 17. The pan rests on the press bed plate 28, which supports the pan during the pressing process.

As demonstrated in FIG. 3, the pan 17 is aligned underneath the punch 1 of the powder press 4 such that the first powder formula 21 aligns with the first region 11 of the punch body 2 and the second powder formula 22 aligns with the second region 12 of the punch body 2. The powder press 4 exerts a ram force downward in the direction of the arrow 41 in order to press the first powder formula 21 and the second powder formula 22 to a given hardness. Specifically, the first region 11 presses on the first powder formula 21 to supply a first predetermined pressure to the first powder formula 21 such that the first formula reaches the given hardness. The second region applies a second predetermined pressure on the second powder formula 22 to achieve the given hardness of that second formula.

The powder press 4 and the punch 1 are configured such that the ram force applied to the punch body results in the first predetermined pressure and the second predetermined pressure, which are the precise pressures necessary to achieve the same given hardness for the first powder formula 21 and the second powder formula 22. The hardness levels of the formulas may be measured, for example, with a penetrometer to determine or verify whether the hardness levels of the formulas contained together in a pan are the same. Then, the configuration of the punch 1, the powder pressing system 60, and/or the method for pressing two cosmetic formulas 62 can be adjusted such that the hardness of the formulas in a pan reach a given hardness. For example, adjustments can be made to the materials used in the regions of the punch and/or the amounts of those materials. Alternatively or additionally, the ram force applied by the press device 5 can be varied.

The given hardness is the hardness level at which each of the powder formulas provides the same payoff performance, which is preferably a predetermined optimal, or desired, payoff performance for the particular powder product, such as a cosmetic product. For example, if the first powder formula 21 and the second powder formula 22 are eye shadows, they preferably each perform in approximately the same way for a user applying the each of the eye shadows with an applicator, and in a way that is predetermined to be desired or optimal.

The punch 1 may be any shape and size configured to press two or more different formulas in a pan 17. In the embodiment of FIGS. 1A-1D, the punch 1 has a punch body 2 in the shape of a square with rounded edges. Such a punch 1 would be appropriate to press a pan of approximately the same shape and surface area as the pressing face 9. In another embodiment depicted in FIGS. 2A-2D, the punch 1 may have a punch body 2 that is cylindrical in shape and having a round pressing face 9. The cylindrical punch body 2 would be most appropriate for pressing powders in a circular pan 17 having approximately the same circular area as the pressing face 9. In still other embodiments, the punch body 2 may take on any shape, such as any polygon.

The two or more regions on the punch 1 may be organized or configured on the punch in any way. For example, in the embodiment of FIGS. 2A and 2B, the punch body 2 is a cylindrical shape having a first region 11 occupying the outer portion of the cylinder and a second region 12 occupying an inner portion of the cylinder. The punch 1 of FIGS. 2A and 2B would be devised to press a circular pan 17 having a second powder formula 22 contained on the inner portion of the circular pan and a first powder formula 21 arranged around the first formula, such that the second powder formula 22 aligns with the second region 12 and the first powder formula 21 aligns with the first region 11 of the punch body 2.

Figure 2A:
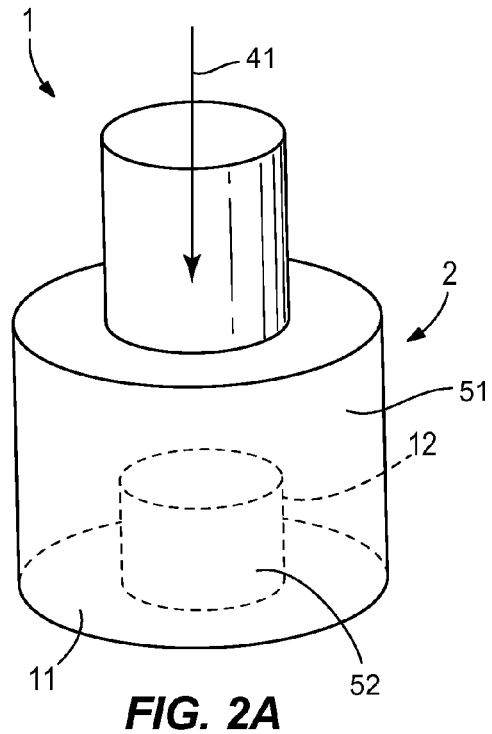
FIG. 2A depicts a side angle view of another embodiment of a punch for pressing two different powder formulas.
Figure 2C:
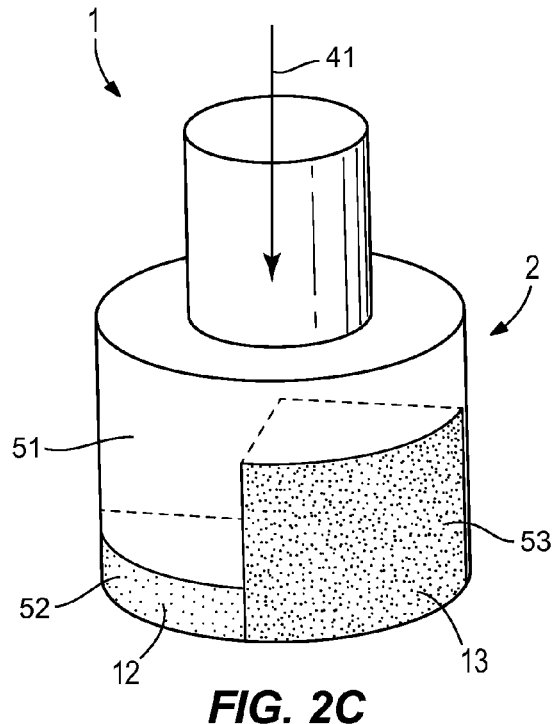
FIG. 2C depicts an embodiment of the punch for pressing three different powder formulas.
Figure 2B:
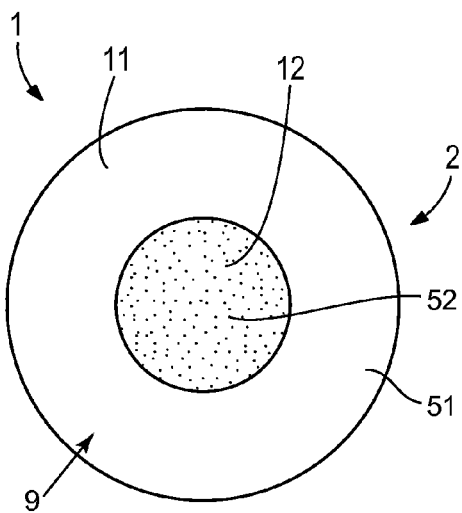
FIG. 2B depicts a bottom view of the embodiment of FIG. 2A.
Figure 2D:
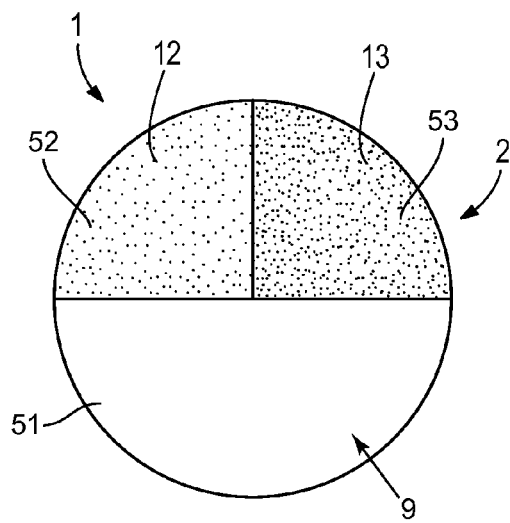
FIG. 2D depicts a bottom view of the embodiment of FIG. 2C.

The punch 1 of FIGS. 2C and 2D has three different regions, including a first region 11, a second region 12 and a third region 13. As previously described, each region is configured to apply a predetermined pressure on a powder formula in order to press that powder formula to a given hardness. More specifically, the first region 22, the second region 12, and the third region 13 are each configured to apply a first predetermined pressure, a second predetermined pressure, and a third predetermined pressure, respectively.

Consistent with the description above, each of the first region 11, second region 12 and third region 13 may be comprised of a different material. More specifically, the first region 11 may be comprised of a first material 51, the second region 12 may be comprised of a second material 52, and the third region 13 may be comprised of a third material 53. Each of the materials 51-53 may be devised to apply a predetermined pressure necessary to achieve a given hardness of a particular formula. In another embodiment, the second material 52 and the third material 53 may be the same material. In such an embodiment, the second region 12 and the third region 13 may have different depths of the material so as to vary the pressures of the second region 12 and the third region 13.

Alternatively or additionally, the depths of the second material 52 of the second region 12 and third material 53 of the third region 13 may be varied to achieve the predetermined pressures necessary to achieve the given hardness of the respective formula. In the embodiment of FIGS. 2C-2D, for example, the depth of the third formula 53 in the third region 13 is significantly greater than the depth of the second material 52 in the second region 12. Thus, in an embodiment where the second material 52 is the same material as the third material 53, the second region 12 of the embodiment of FIG. 2C would have a greater predetermined pressure than the third region 13. However, the resulting pressure of each region may depend on the materials used for that region. For example, if the second material 52 was significantly softer than the third material 53, the third region 13 could apply a greater predetermined pressure than that applied by the second region 12.

The embodiment of FIGS. 2C and 2D would be appropriate for pressing a circular pan 17 having three different formulas arranged analogously to the first region 11, second region 12, and third region 13 of the punch body 2. The three formulas are arranged in an undivided fashion when pressed by the punch 1, such that the formulas are immediately adjacent to one another without any physical divider separating the formulas.

As described above, it is desirable that all formulas contained within a pan yields the same payoff during use, which is achieved when the formulas reach a given hardness. In order to apply the different predetermined pressures to achieve a given hardness of each of the formulas in the pan, the materials of the first region 11 and the second region 12, as well as the third region 13 and/or any additional regions of the punch body 2 must be chosen and/or accounted for within the powder press method and system. As described above, the first region 11 may be comprised of a first material 51 that is harder than the second material 52 of the second region 12. Accordingly, the first region 11 will be used to press a formula requiring a higher predetermined pressure to achieve a given hardness than the adjacent material or materials in the pan.

Conversely, the second material 52 comprising at least a portion of a second region 12 is less hard than that of the first material 51 and thus would be used to press a material requiring a lower predetermined pressure to achieve a given hardness than the adjacent formula pressed by the first region 11.

Each of the first powder formula 21, the second powder formula 22, and any additional formula in the pan, may be a different formula or product from one another, having different textures with different amounts of caking or pressing agents. Thus, each formula may require a different pressure in order to achieve a given hardness that will yield the best payoff for that formula. For example, in one embodiment the first powder formula 21 may be a pearl powder formula, while the second powder formula 22 may be a matte powder formula. Since pearl formulas generally contain less caking agents per unit volume than matte formulas, the pearl formula will require a higher predetermined pressure in order to achieve the given hardness. Likewise, since matte powder formulas generally contain more caking agents than pearl formulas, the predetermined pressure required to achieve the given hardness of the matte shade will be less.

In a preferred embodiment, the hardness of each of the pressed first powder formula 21 and the pressed second powder formula 22 is the same given hardness so that each of the powder formulas within the pan perform similarly for the user. Furthermore, it is important to not over-press or under-press any formula within a pan. Over-pressing, or applying too high of an applied pressure, can cause glazing of the product which yields a product that is too hard to provide optimum usefulness to the user. Under-pressing a product, or applying too little of an applied pressure, yields a product that is prone to dusting and breaking up during transit or use.

The first material 51 may be any material that is harder than the second material 52. Likewise, the second material 52 may be any material that is less hard than the first material 51. In one embodiment, the first material 51 may be a steel, such as a cold-rolled steel or a low-carbon steel, and the second material 52 may be any material less hard than steel. For example, the second material 52 may be made of Teflon, plastic, or some type of rubber. In one embodiment, the second material 52 may be neoprene rubber, a silicone rubber, or a gum rubber. In still other embodiments, the first material 51 may be something less hard than steel, such as iron, a platinum alloy, an aluminum alloy, or some other metal or alloy. In fact, the first material 51 may even be a softer material, such as a rubber, as long as the second material 52 is even softer, or less hard, than the first material 51.

Figure 4:
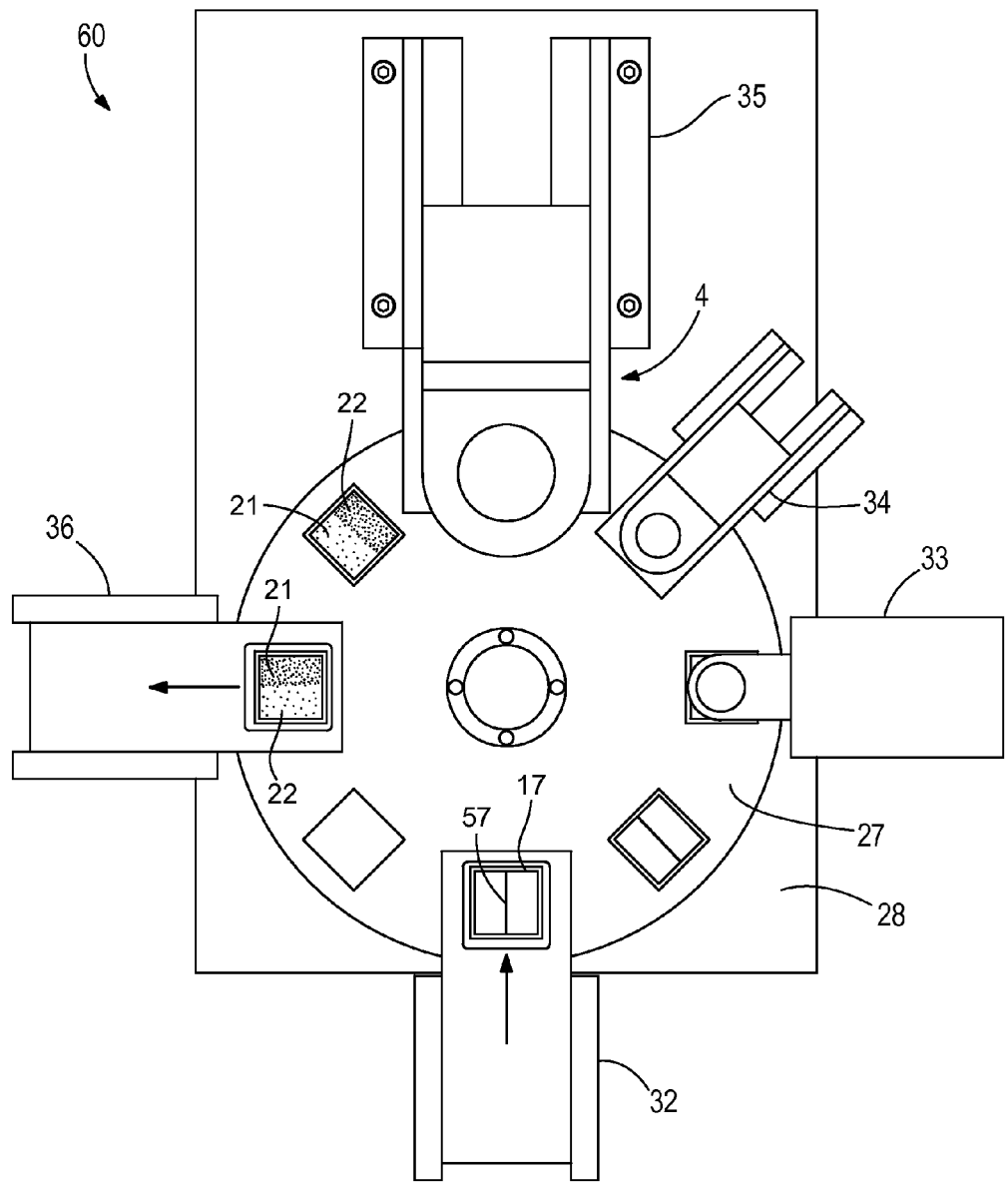
FIG. 4 depicts an embodiment of a system and method for simultaneously pressing two or more different cosmetic formulas.
Figure 5:
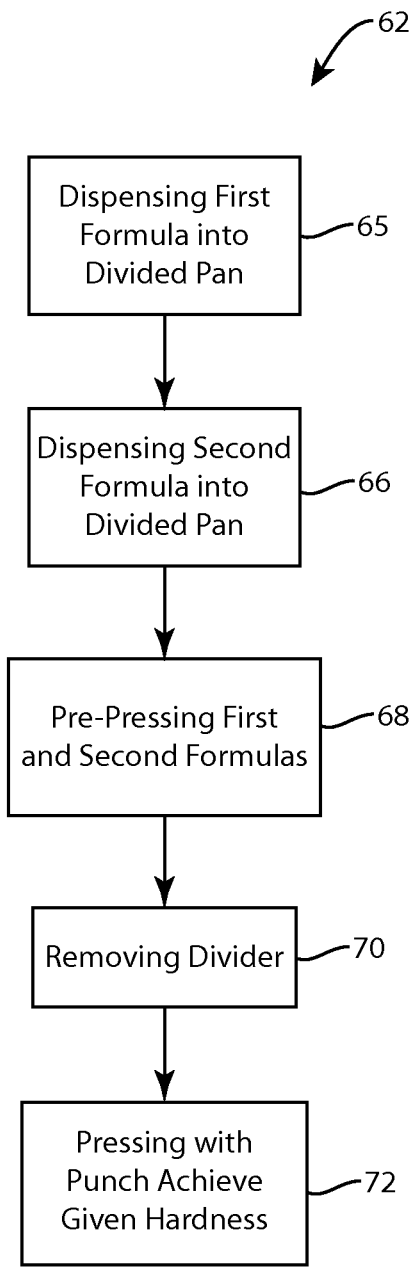
FIG. 5 depicts an embodiment of a method for simultaneously pressing two or more different cosmetic formulas.

Turning to FIG. 4, a powder pressing system 60 includes a pan loading station 32, powder dispensing station 33, pre-pressing station 34, pressing station 35 (which includes powder press 4), and pan unloading station 36. The powder pressing system 60 of FIG. 4 further comprises a die plate 27 for containing and moving pans from one station to another, as well as a press bed plate 28 for supporting the pans as they are moved throughout the system 60. The powder press 4 of the system 60 incorporates a punch for simultaneously pressing two or more different powder formulas, such that the powder press system 60 is enabled to simultaneously press multiple cosmetic formulas in a single pan.

The pan loading station 32 may be positioned to load empty containers onto the die plate 27. The loading station may include any loading mechanism known in the art for loading containers onto a die plate 27, or rotary cable or conveying system. For example, one exemplary loading mechanism may be a PLC-controlled (programmable logic controller-controlled) pick and place mechanism or a computer-controlled robotic arm loading system. Alternatively, the pan loading station may not include any automated loading mechanism, but may be a person loading empty pans onto the die plate 27 at the pan loading station 32.

In the embodiment of FIG. 4, the die plate 27 rotates in a counterclockwise direction. Thus, after the pan is loaded onto the die plate 27 at the pan loading station 32, the die plate 27 rotates to move the pan 17 through the system 60 such that it travels from the insertion point at the pan loading station 32 to the powder dispensing station 33, where two or more powders are inserted into the pan, to the pre-pressing station 34, where the loose powders are initially pressed, to the pressing station 35, where the pre-pressed powders are pressed to a given hardness using powder press 4 containing a punch for simultaneously pressing two or more different powder formulas, to the pan unloading station 36 where the filled pan 17 is unloaded off of the die plate 27.

The powder dispensing station 33 may include any powder dispenser or any number of powder dispensers capable of dispensing any loose powder, such as a cosmetic powder, into the pan 17. In one embodiment, the powder dispensing station 33 may have one or more hoppers containing powder formulas. The hoppers may have a rake that spins within the hopper to push out a measured amount of flowable powder into the pan 17. The powder dispensing station 33 may be configured to dispense two or more powder formulas into the same pan 17. Alternatively, multiple dispensing stations 33 may be incorporated into the system 60, each dispensing a single powder formula into the pan separately at each station.

In one embodiment, the pan 17 is initially configured with at least one removable divider 57. The removable divider 57 is configured to initially separate the various powder formulas in the pan while they are in the loose powder form. The removable divider 57 may be configured to accommodate and separate any number of formulas placed in a single pan 17. Alternatively, multiple removable dividers 57 may be used in a single pan 17 to divide multiple formulas.

The removable divider 57 may be placed into the pan prior to loading the pan 17 onto the die plate 27 at the pan loading station 32. Alternatively, the removable divider 57 may be inserted into the pan 17 at the pan loading station 32, or at the powder dispensing station 33, or at any point therebetween. The removable divider 57 may remain in the pan 17 until after the powder has been pre-pressed at pre-pressing station 34. The purpose of the pre-press is to press each formula such that it is no longer in a loose powder and will maintain its general form when the removable divider 57 is removed from between the formulas. However, the pre-press does not press the powder formulas to the given hardness level reached by the powder press 4 at the main pressing stage.

In the embodiment of FIG. 4, the powder dispensing station 33 dispenses a first powder formula 21 into one side of the removable divider 57 and a second powder formula 22 into a second side of the removable divider in the pan 17. The rotary table 27 then moves that pan 17 filled with the dispensed powder formula 21 and the second powder formula 22 in loose powder form to the pre-pressing station 34. At the pre-pressing station 34, the first powder formula 21 and the second powder formula 22 are pre-pressed so that each formula achieves an initial hardness that presses the loose powder into a hard enough form that the removable divider 57 can be removed without causing significant shift or mixing of the first powder formula 21 and the second powder formula 22.

The pre-pressing station may include any press capable of pressing the formulas into an initial hardness. For example, the pre-press may be a single stroke mechanical or hydraulic press. The pre-press may use a separate pressing step for each formula in the pan. Alternatively, the pre-press may simultaneously press the first powder formula 21 and the second powder formula 22 to achieve the initial hardness of each formula. In such an embodiment, the pre-press would need to accommodate the removable divider 57 positioned between the formulas. For example, the pre-press may have a separate punch body to compress each formula. Alternatively, the pre-press may use a single punch body configured to accommodate the removable divider 57.

The removable divider 57 is then removed from the pan 17 after the formulas have been pre-pressed. The removable divider 57 may be removed at the pre-pressing station 34, prior to the pan being moved to the pressing station 35. Alternatively, the removable divider 57 may be removed from the pan 17 at the pressing station 35 prior to the final press by powder press 4. In still other embodiments, the removable divider 57 may be removed anywhere in the process between the pre-press at the pre-pressing station 34 and the final press with punch 1 at the pressing station 35.

As described above, the powder press 4 presses the two or more powder formulas in the pan 17 to a given hardness using the punch 1 for simultaneously pressing two or more different powder formulas. After that step, the pan 17 containing the pressed powder formulas is moved to the pan unloading station 36 by the die plate 27. The pan unloading station may include any unloading mechanism known in the art for unloading filled containers from a die plate, rotary cable, conveying system, etc. In one exemplary embodiment, the unloading mechanism is capable of accurately picking up filled containers 17 from the die plate 27 and placing them on a separate conveying system with a high level of repeatability. Alternatively, the unloading mechanism may be a person tasked with unloading the filled pan 17 at the unloading station 36. It should be understood that the same or similar process could be carried out using a line-type system, such as a system employing a conveyor instead of a rotary table.

An embodiment of a method 62 for pressing two or more cosmetic formulas contained in the same pan includes dispensing a first powder formula into a divided pan at step 65 and dispensing a second powder formula into the divided pan at step 66. The first powder formula is dispensed into one side of the divider in the divided pan, and the second powder formula is dispensed into the opposing side of the divider. The first powder formula and the second powder formula are in loose powder form.

At step 68, the powder is pre-pressed to achieve an initial hardness level such that the divider can be removed from the pan without significantly disturbing the first powder formula or the second powder formula, or allowing the formulas to shift or mix. The divider between the formulas is then removed at step 70. At step 72, the first powder formula and the second powder formula are pressed with a punch. The punch has a punch body with a first region comprised of a first material and a second region comprised of a second material. The first region is configured to press the first formula and the second region is configured to press the second formula. For example, the first and second regions may be configured to press the first and second formulas to a given hardness, as is thoroughly described herein, such that the pressing step 72 is carried out to achieve a given hardness level of the first powder formula and the second powder formula.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A punch for simultaneously pressing two or more different powder formulas, the punch comprising:
   a punch body having:
     a first region comprised of a first material and configured to apply a first predetermined pressure to a first powder formula when a ram force is placed on the punch body,
     a second region at least partially comprised of a second material and configured to apply a second predetermined pressure to a second powder formula when the ram force is placed on the punch body; and
     wherein the second material is less hard than the first material such that the second predetermined pressure is less than the first predetermined pressure.

2. The punch of claim 1 wherein the first region is immediately adjacent to the second region such that the punch body is configured to press a pan containing both the first powder formula and the second powder formula in an undivided fashion.

3. The punch of claim 1 wherein the first predetermined pressure is the pressure necessary to achieve a given hardness of the first powder formula and the second predetermined pressure is the pressure necessary to achieve the given hardness of the second powder formula.

4. The punch of claim 3 wherein the second region has a depth of the second material configured to provide the second predetermined pressure when the ram force is placed on the punch body.

5. The punch of claim 1 wherein the first material is low-carbon steel.

6. The punch of claim 5 wherein the second material is a rubber material.

7. The punch of claim 6 wherein the second material is one of a neoprene rubber, a gum rubber, and a silicon rubber.

8. The punch of claim 5 wherein the second material is comprised of a synthetic resin.

9. The punch of claim 1, the punch body further having a third region comprised of a third material and configured to apply a third predetermined pressure to a third powder formula when the ram force is placed on the punch body.

10. A cosmetic powder press for simultaneously pressing at least two different cosmetic formulas, the cosmetic powder press comprising:
    a press device having a press ram and configured to exert a ram force; and
    a punch body positioned at the end of the press ram, the punch body having:
      a first region comprised of a first material and configured to apply a first predetermined pressure to a first powder formula when the ram force is exerted on the punch body;
      a second region comprised of a second material and configured to apply a second predetermined pressure to a second powder formula when the ram force is exerted on the punch body; and
      wherein the second material is less hard than the first material such that the second predetermined pressure is less than the first predetermined pressure.

11. The punch of claim 10 wherein the first predetermined pressure is the pressure necessary to achieve a given hardness of the first powder formula and the second predetermined pressure is the pressure necessary to achieve the given hardness of the second powder formula.

12. The powder press of claim 11 wherein the first powder formula is a pearl cosmetic powder and the second powder formula is a matte cosmetic powder.

13. The powder press of claim 10 wherein the second region has a depth of the second material configured to provide the second predetermined pressure when the ram force is placed on the punch body.

14. The powder press of claim 10 wherein the first region is comprised of low-carbon steel and the second region is comprised of neoprene rubber, wherein the neoprene rubber has a depth configured to provide the second predetermined pressure when the ram force is placed on the punch body.

15. The powder press of claim 10 wherein the first region is immediately adjacent to the second region such that the punch body is configured to press a pan containing both the first powder formula and the second powder formula in an undivided fashion.

16. The powder press of claim 10 wherein the press is a hydraulic press or a mechanical press.

17. A method of pressing two or more different cosmetic formulas contained adjacently in the same pan, the method comprising:
    dispensing a first powder formula into a first side of a divider in a pan;
    dispensing a second powder formula into a second side of the divider in the pan;
    pre-pressing the first powder formula and the second powder formula;
    removing the divider from the pan such that the first powder formula and the second powder formula are immediately adjacent to one another;
    pressing the first powder formula and the second powder formula in the pan with a punch body, the punch body having:
      a first region comprised of a first material and configured to press the first formula;
      a second region comprised of a second material and configured to press the second formula; and
      wherein the second material is less hard than the first material.

18. The method of claim 17 further comprising pressing the first powder formula and the second powder formula to achieve a given hardness of the first powder formula and a second powder formula.

19. The method of claim 18 wherein the first region is configured to apply a first predetermined pressure to the first powder formula and the second region is configured to apply a second predetermined pressure to the second powder formula;
    wherein the first predetermined pressure is the pressure necessary to achieve the given hardness of the first powder formula and the second predetermined pressure is the pressure necessary to achieve the given hardness of the second powder formula.

20. The method of claim 19 wherein the first material is steel and the second material is rubber, and wherein the first powder formula is a pearl cosmetic powder and the second powder formula is a matte cosmetic powder.

* * * * *